(12) United States Patent
Koslow

(10) Patent No.: US 7,011,753 B2
(45) Date of Patent: Mar. 14, 2006

(54) MICROPOROUS FILTER MEDIA, FILTRATION SYSTEMS CONTAINING SAME, AND METHODS OF MAKING AND USING

(76) Inventor: Evan E. Koslow, 14 Twelve O'Clock Rd., Weston, CT (US) 06883

( * ) Notice: Subject to any disclaimer, the term of this patent is extended or adjusted under 35 U.S.C. 154(b) by 291 days.

(21) Appl. No.: 10/442,314

(22) Filed: May 20, 2003

(65) Prior Publication Data

US 2003/0205529 A1 Nov. 6, 2003

Related U.S. Application Data

(62) Division of application No. 10/286,695, filed on Nov. 1, 2002, now Pat. No. 6,835,311.
(60) Provisional application No. 60/354,062, filed on Jan. 31, 2002.

(51) Int. Cl.
*B01D 33/46* (2006.01)

(52) U.S. Cl. .................. 210/263; 210/505; 210/508; 210/489; 210/502.1

(58) Field of Classification Search ............ 210/263, 210/265, 503, 505, 508, 509, 502.1, 257.2, 210/243, 489, 492, 268; 55/524
See application file for complete search history.

(56) References Cited

U.S. PATENT DOCUMENTS

| | | | | |
|---|---|---|---|---|
| 4,126,832 A | * | 11/1978 | Schlossberg et al. | 372/4 |
| 4,366,068 A | * | 12/1982 | Ostreicher et al. | 210/767 |
| 5,302,249 A | * | 4/1994 | Malhotra et al. | 162/135 |
| 5,817,325 A | * | 10/1998 | Sawan et al. | 424/411 |
| 5,972,501 A | * | 10/1999 | Ohmory et al. | 428/370 |
| 6,034,010 A | * | 3/2000 | Cartwright et al. | 442/417 |
| 6,126,931 A | * | 10/2000 | Sawan et al. | 424/78.09 |
| 6,180,584 B1 | * | 1/2001 | Sawan et al. | 510/382 |
| 6,254,748 B1 | * | 7/2001 | Surampudi et al. | 204/422 |
| 6,284,680 B1 | * | 9/2001 | Aikawa et al. | 442/363 |
| 6,340,663 B1 | * | 1/2002 | Deleo et al. | 510/438 |
| 6,387,415 B1 | * | 5/2002 | Garris | 424/618 |
| 6,395,235 B1 | * | 5/2002 | Kilcoin et al. | 422/103 |
| 6,413,368 B1 | * | 7/2002 | Dwiggins et al. | 162/101 |
| 6,426,383 B1 | * | 7/2002 | Fong et al. | 524/827 |
| 6,440,405 B1 | * | 8/2002 | Cooper et al. | 424/78.17 |
| 6,451,260 B1 | * | 9/2002 | Dusterhoft et al. | 422/68.1 |
| 6,469,120 B1 | * | 10/2002 | Elfersy et al. | 528/29 |
| 6,471,876 B1 | * | 10/2002 | Hansen et al. | 210/764 |
| 6,500,302 B1 | * | 12/2002 | Dwiggins et al. | 162/101 |
| 6,518,479 B1 | * | 2/2003 | Graef et al. | 604/383 |
| 6,525,240 B1 | * | 2/2003 | Graef et al. | 604/383 |
| 6,531,078 B1 | * | 3/2003 | Laine et al. | 264/86 |
| 6,565,749 B1 | * | 5/2003 | Hou et al. | 210/500.38 |
| 6,630,016 B1 | * | 10/2003 | Koslow | 95/285 |
| 6,835,311 B1 | * | 12/2004 | Koslow | 210/490 |

FOREIGN PATENT DOCUMENTS

| | | | |
|---|---|---|---|
| EP | 0251783 | * | 1/1987 |
| JP | 2000178875 | * | 6/2000 |
| WO | WO 97/23594 | * | 7/1997 |
| WO | WO 0107090 | * | 2/2001 |
| WO | WO 01/93991 | * | 12/2001 |

* cited by examiner

*Primary Examiner*—Ana Fortuna
(74) *Attorney, Agent, or Firm*—Shirley S. Ma; Gary L. Warner

(57) ABSTRACT

The invention is directed to a microbiological interception enhanced filter medium, preferably having an adsorbent prefilter located upstream from the filter medium. Preferably, the prefilter is adapted to remove natural organic matter in an influent prior to the influent contacting the microbiological interception enhanced filter medium, thereby preventing loss of charge on the filter medium. The microbiological interception enhanced filter medium is most preferably comprised of fibrillated cellulose fibers, in particular, lyocell fibers. At least a portion of the surface of the at least some of the fibers have formed thereon a microbiological interception enhancing agent comprising a cationic metal complex. A filter medium of the present invention provides greater than about 4 log viral interception, and greater than about 6 log bacterial interception.

6 Claims, 4 Drawing Sheets

МICROPOROUS FILTER MEDIA, FILTRATION SYSTEMS CONTAINING SAME, AND METHODS OF MAKING AND USING

This application is a divisional application of U.S. patent application Ser. No. 10/286,695 filed on 1 Nov. 2002, now U.S. Pat. No. 6,835,311, which claims priority from U.S. Provisional Application Ser. No. 60/354,062 filed on 31 Jan. 2002.

The present invention is directed to filter media having microbiological interception capability, filtration systems containing such filter media, and methods of making and using same.

Modern consumer water filters often provide "health claims" including reduction of particulates, heavy metals, toxic organic chemicals, and select microbiological threats. These filtration systems have been able to intercept microorganisms such as Cryptosporidium and Giardia using roughly 1.0 micron structures. However, in order to provide microbiological interception of even smaller microbiological threats such as viruses, a filter medium having a submicron microporous structure is required. Prior art filtration systems often attempt to achieve broad microbiological interception using filter media with insufficiently small pore size and with poor physical integrity. The balance between the necessary pore structure required for successful microbiological interception and satisfactory filter performance has not been achieved. In addition, prior art systems did not provide devices capable of operating in the presence of "interferences" consisting of substances that cause a loss of filtration performance.

SUMMARY OF THE INVENTION

The present invention is directed to, in a first aspect, a filter medium comprising: a microporous structure having a mean flow path of less than or equal to about 1 micron; and a microbiological interception enhancing agent comprising a cationic metal complex capable of imparting a positive charge on at least a portion of the microporous structure.

In another aspect, the present invention is directed to a composite filter medium comprising: an adsorbent prefilter having immobilized therein a material capable of removing charge-reducing contaminants; a microporous structure, disposed downstream from the adsorbent layer, comprising a plurality of nanofibers, the microporous structure having a mean flow path of less than about 0.6 micron; and a microbiological interception enhancing agent comprising a silver-cationic material-halide complex having a high charge density, coated on at least a portion of a surface of at least some of the plurality of fibers of the fiber matrix.

In yet another aspect, the present invention is directed to a filter system comprising: a granular bed of particles capable of removing charge-reducing contaminants; a microporous structure, disposed downstream from the granular bed, having a mean flow path of less than about 0.6 micron; and a microbiological interception enhancing agent comprising a silver-cationic material-halide complex having a high charge density, coated on at least a portion of a surface of the microporous structure.

In still yet another aspect, the present invention is directed to a filter system comprising: a solid composite block comprising a material capable of removing charge-reducing contaminants; a microporous structure, disposed downstream from the block, having a mean flow path of less than about 2.0 microns; and a microbiological interception enhancing agent comprising a silver-cationic material-halide complex having a high charge density, coated on at least a portion of a surface of the microporous structure.

In still yet another aspect, the present invention is directed to a process of making a filter medium comprising the steps of: providing a microporous structure having a mean flow path of less than about 1 micron; and coating at least a portion of the microporous structure with a microbiological interception enhancing agent, the microbiological interception enhancing agent comprising a cationic metal complex capable of imparting a positive charge on at least a portion of the microporous structure.

In a further aspect, the present invention is directed to a process for making a filter medium comprising the steps of: providing a plurality of nanofibers; coating at least a portion of a surface of at least some of the plurality of nanofibers with a microbiological interception enhancing agent, the microbiological intercepting agent comprising a cationic metal complex; and forming the fibers into a microporous structure having a mean flow path of less than about 1 micron.

In still a further aspect, the present invention is directed to a process for making a filter medium comprising the steps of: providing a plurality of polymer nanofibers; coating at least a portion of a surface of at least some of the plurality of polymer nanofibers with a microbiological interception enhancing agent, the microbiological intercepting agent comprising a cationic metal complex; and forming a microporous structure having a mean flow path of less than about 1 micron.

In still a further aspect, the present invention is directed to a process for making a filter medium comprising the steps of: providing a plurality of cellulose nanofibers; coating at least a portion of a surface of at least some of the plurality of cellulose fibers with a microbiological interception enhancing agent, the microbiological intercepting agent comprising a cationic metal complex; and forming a microporous structure having a mean flow path of less than about 1 micron.

In still yet a further aspect, the present invention is directed to a process of making a filter medium comprising the steps of: providing a membrane having a mean flow path of less than about 1 micron; and coating at least a portion of the membrane with a microbiological interception enhancing agent, the microbiological interception enhancing agent comprising a cationic metal complex capable of imparting a positive charge on at least a portion of the membrane.

In still yet a further aspect, the present invention is directed to a process for making a filter medium comprising the steps of: providing a plurality of nanofibers; coating at least a portion of a surface of at least some of the plurality of the nanofibers with a microbiological interception enhancing agent, the microbiological intercepting agent comprising a silver-amine-halide complex having a medium to high charge density and a molecular weight greater than 5000 Daltons; and forming a microporous structure having a mean flow path of less than or about 0.6 microns.

In still yet a further aspect, the present invention is directed to a process for making a filter system comprising the steps of: providing an adsorbent prefilter comprising a material capable of removing charge-reducing contaminants from an influent, wherein the material is immobilized into a solid composite block; providing a plurality of nanofibers; coating at least a portion of a surface of at least some of the plurality of the nanofibers with a microbiological interception enhancing agent, the microbiological intercepting agent comprising a silver-amine-halide complex having a medium to high charge density and a molecular weight greater than 5000 Daltons; and forming a microporous structure having a mean flow path of less than or about 0.6 microns.

In still yet a further aspect, the present invention is directed to a method of removing microbiological contaminants in a fluid comprising the steps of: providing a filter medium having a microporous structure having a mean flow path of less than about 1 micron, the microporous structure having coated on at least a portion thereof a microbiological interception enhancing agent comprising a cationic metal complex wherein the cationic material has a medium to high charge density and a molecular weight greater than about 5000 Daltons; contacting the fluid to the filter medium for greater than about 3 seconds; and obtaining at least about 6 log reduction of microbiological contaminants smaller than the mean flow path of the filter medium, that pass through the filter medium.

In still yet a further aspect, the present invention is directed to a gravity-flow filtration system for treating, storing, and dispensing fluids comprising: a first reservoir for holding a fluid to be filtered; a filter medium in fluid communication with the first reservoir, the filter medium comprising a microporous structure with a mean flow path of less than about 1 micron, and wherein the filter medium is so treated as to provide at least about 4 log reduction of microbiological contaminants smaller than the mean flow path of the filter medium; and a second reservoir in fluid communication with the filter medium for collecting a filtered fluid.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the description of the preferred embodiment(s) that follows taken in conjunction with the accompanying drawings in that:

DETAILED DESCRIPTION OF THE INVENTION

Figure 1:
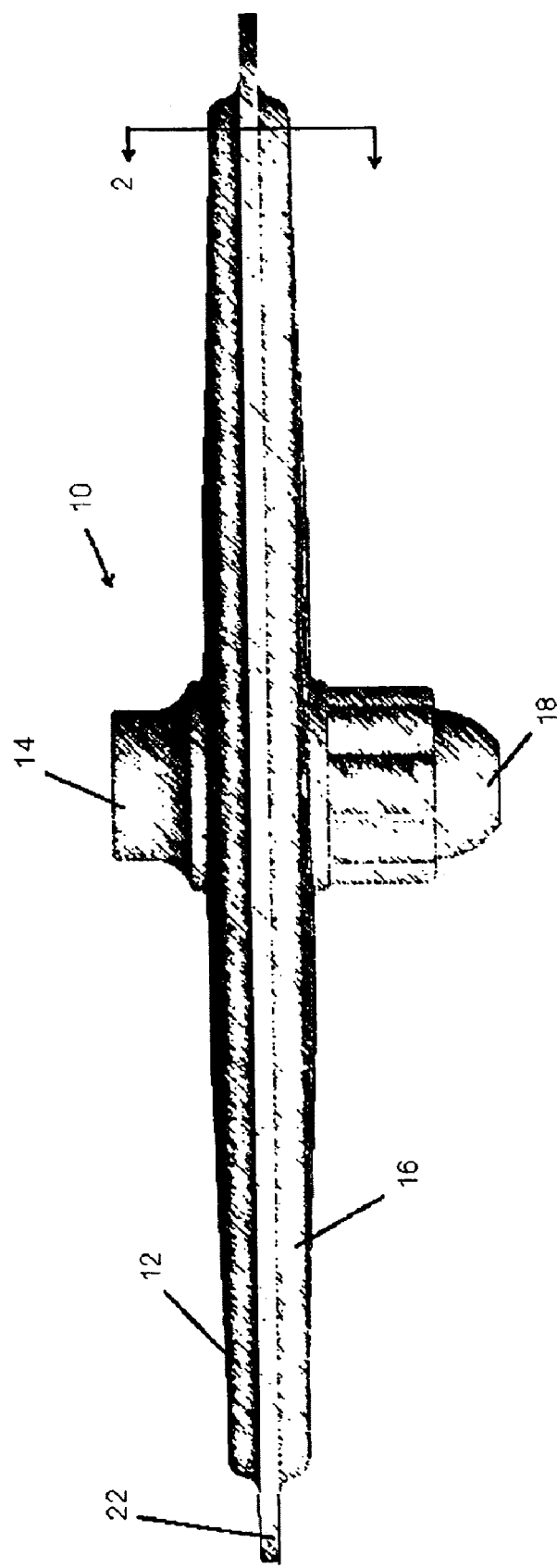
FIG. 1 is a side plan view of a filter incorporating the filter media of the present invention.

In describing the preferred embodiment of the present invention, reference will be made herein to FIGS. 1 to 4 of the drawings in that like numerals refer to like features of the invention. Features of the invention are not necessarily shown to scale in the drawings.

Definitions

As used herein, "absorbent" shall mean any material that is capable of absorbing impurities primarily by drawing the impurities into its inner structure.

As used herein, "adsorbent" shall mean any material that is capable of adsorbing impurities primarily by physical adsorption to its surface.

As used herein, "adsorbent filter medium" or "adsorbent prefiltration medium" shall mean a filter medium made with an adsorbent such as, for example, activated carbon. Exemplary of an adsorbent filter medium is PLEKX®, commercially available from KX Industries, L.P. of Orange, Conn.

As used herein, "binder" shall mean a material used principally to hold other materials together.

As used herein, "Canadian Standard Freeness" or "CSF" shall mean a value for the freeness or drainage rate of pulp as measured by the rate that a suspension of pulp may be drained. This methodology is well known to one having skill in the paper making arts.

As used herein, "composite filter medium" shall mean a filter medium that combines a prefilter, an adsorbent prefiltration medium, and the microbiological interception enhanced filter medium of the present invention, into a single composite structure. In some cases, the prefilter may be absent or its function assumed by the adsorbent prefiltration medium.

As used herein, "contaminant reduction" shall mean attenuation of an impurity in a fluid that is intercepted, removed, or rendered inactive, chemically or biologically, in order to render the fluid safer as, for example for human use, or more useful, as in industrial applications.

As used herein, "fiber" shall mean a solid that is characterized by a high aspect ratio of length to diameter of, for example, several hundred to one. Any discussion of fibers includes whiskers.

As used herein, "filter medium" shall mean a material that performs fluid filtration.

As used herein, "fluid" shall mean a liquid, gas, or combination thereof.

As used herein, "forming" shall mean converting a loose, unstructured substance into a cohesive, uniform structure. For example, the conversion of loose fibers into a paper.

As used herein, "intercept" or "interception" are taken to mean interfering with, or stopping the passage of, so as to affect, remove, inactivate or influence.

As used herein, "log reduction value" or "LRV" shall mean the $\log_{10}$ of the number of organisms in the influent divided by the number of organisms in the effluent of a filter.

As used herein, "membrane" shall mean a porous medium wherein the structure is a single continuous solid phase with a continuous pore structure.

As used herein, "microbiological interception enhanced filter medium" shall mean a filter medium having a microporous structure where at least a portion of its surface is treated with a microbiological interception enhancing agent.

As used herein, "microorganism" shall mean any living organism that may be suspended in a fluid, including but not limited to bacteria, viruses, fungi, protozoa, and reproductive forms thereof including cysts and spores.

As used herein, "microporous structure" shall mean a structure that has a mean flow path less than about 2.0 microns, and often less than about 1.0 micron.

As used herein, "nanofiber" shall mean a fiber having a diameter less than about 3.0 millimeters.

As used herein, "natural organic matter" or "NOM" shall mean organic matter often found in potable or non-potable water, a portion of which reduces or inhibits the zeta potential of a positively charged filter medium. Exemplary of NOM are polyanionic acids such as, but not limited to, humic acid and fulvic acid.

As used herein, "nonwoven" means a web or fabric or other medium having a structure of individual fibers that are interlaid, but not in a highly organized manner as in a knitted or woven fabric. Nonwoven webs generally may be prepared by methods that are well known in the art. Examples of such processes include, but are not limited to, and by way of illustration only, meltblowing, spunbonding, carding, and air laying.

As used herein, "paper" or "paper-like" shall mean a generally flat, fibrous layer or mat of material formed by a wet laid process.

As used herein, "particle" shall mean a solid having a size range from the colloidal to macroscopic, and with no specific limitation on shape, but generally of a limited length to width ratio.

As used herein, "prefilter" shall mean a filter medium generally located upstream from other filtration layers, structures or devices and capable of reducing particulate contaminants prior to the influent contacting subsequent filtration layers, structures or devices.

As used herein, "sheet" shall mean a roughly two-dimensional structure having a length and a width that are significantly greater than its thickness.

As used herein, "whisker" shall mean a filament having a limited aspect ratio and intermediate between the aspect ratio of a particle and a fiber. Any discussion of fibers includes whiskers.

The Microbiological Interception Enhanced Filter Medium

A filter medium of the present invention includes a microporous structure that provides microbiological interception capability using a combination of an appropriate pore structure and a chemical treatment. The microporous structure comprises any material that is capable of having a mean flow path of less than about 2.0 microns. Preferably, the microporous structure comprises nanofibers formed into a nonwoven or paper-like structure, but may include whiskers, or be a membrane. The tight pore structure of the microbiological interception enhanced filter medium of the present invention provides short diffusion distances from the fluid to the surface of the filter medium. The chemical treatment process used to treat the surface of the microporous structure utilizes a synergistic interaction between a cationic material and a biologically active metal, that when combined, provide broad-spectrum reduction of microbiological contaminants on contact. The charge provided by the cationic material to the filter medium aids in electro-kinetic interception of microbiological contaminants, while the tight pore structure provides a short diffusion path and, therefore, rapid diffusion kinetics of contaminants in a flowing fluid to the surface of the microporous structure. The microporous structure also provides supplemental direct mechanical interception of microbiological contaminants. Due to the dominant role of diffusion for the interception of extremely small particles, there is a direct correlation between the log reduction value of viral particles and the contact time of the influent within the filter medium, rather than a dependence upon the thickness of the filter medium.

Characteristics of the Microbiological Interception Enhanced Filter Medium

In order to provide full microbiological interception capability, the microbiological interception enhanced filter medium of the present invention has a mean flow path of less than about 2 microns, and preferably less than or equal to about 1 micron, and more preferably less than or equal to about 0.6 microns. The volume of the microbiological interception enhanced filter medium of the present invention compared to the flow rate of fluid through the filter medium must be sufficient to provide a contact time adequate for the contaminants to diffuse to the surface of the filter medium. To provide enhanced electro-kinetic interception of microorganisms, of which the majority are negatively charged, under most conditions, the microbiological interception enhanced filter medium has a positive zeta potential generally greater than about +10 millivolts at pH values of about 6 to about 7, and retains a net positive zeta potential at pH values of about 9 or greater.

Natural organic matter (NOM), such as polyanionic acids, i.e., humic acid or fulvic acid, that may reduce or remove the charge on the microbiological interception enhanced filter medium, is preferably prevented from contacting the charged microporous structure through the use of an adsorbent prefilter that substantially removes the NOM. When used in the context of a gravity-flow water filtration system, it is preferable that the microbiological interception enhanced filter medium be made with hydrophilic materials to provide good, spontaneous wettability. Alternatively, in other applications, the microbiological interception enhanced filter medium may be treated to provide either a hydrophilic or hydrophobic characteristic as needed. It is possible that the microbiological interception enhanced filter medium can have both positively and negatively charged and uncharged regions, and/or hydrophilic and hydrophobic regions. For example, the negatively charged regions can be used to enhance the interception of less common positively charged contaminants and uncharged hydrophobic regions can be used to provide enhanced interception of contaminants that are attracted to hydrophobic surfaces.

The Fibers/Whiskers or Particulate Ingredients

The microbiological interception enhanced filter medium of the present invention includes a microporous structure that may include a plurality of nanofibers, including whiskers or micro-particulate ingredients, of organic and inorganic materials including, but not limited to, polymers, ion-exchange resins, engineered resins, ceramics, cellulose, rayon, ramie, wool, silk, glass, metal, activated alumina, carbon or activated carbon, silica, zeolites, diatomaceous earth, activated bauxite, fuller's earth, calcium hydroxyappatite, other adsorbent materials, or combinations thereof. Combinations of organic and inorganic fibers and/or whiskers or micro particulates are contemplated and within the scope of the invention as for example, glass, ceramic, or metal fibers and polymeric fibers may be used together with very small particles incorporated into the microporous structure.

When produced by a wet laid process from nanofibers such as cellulose or polymer fibers, such fibers should also have a Canadian Standard Freeness of less than or equal to about 100, and most preferably less than or equal to about 45. Preferably, a significant portion of the fibers should have a diameter less than or equal to about 1000 nanometers, more preferably less than or equal to about 400 nanometers, and fibers less than or equal to about 250 nanometers in diameter are most preferred. It is preferable to chop the fibers to a length of about 1 millimeter to about 8 millimeters, preferably about 2 millimeters to about 6 millimeters, and more preferably about 3 millimeters to about 4 millimeters. Fibrillated fibers are most preferred due to their exceptionally fine dimensions and potentially low cost.

Preferably, fibrillated synthetic cellulose fibers, processed in accordance with the present invention, can produce an ultra-fine, hydrophilic microporous structure for use as the microbiological interception enhanced filter medium of the present invention. Such fibrillated cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell are often curled. The curls provide a significant amount of fiber entanglement, resulting in a finished filter medium with high dry strength and significant residual wet strength. Furthermore, the fibrillated lyocell fibers may be produced in large quantities using equipment of modest capital cost. It will be understood that fibers other than cellulose may be fibrillated to produce extremely fine fibrils, such as for example, artificial fibers, in particular, acrylic or nylon fibers, or other natural cellulosic materials. Combinations of fibrillated and non-fibrillated fibers may be used in the microporous structure.

Membranes

The microbiological interception enhanced filter medium of the present invention can comprise a membrane of organic or inorganic composition including, but not limited to, polymers, ion-exchange resins, engineered resins, ceramics, cellulose, rayon, ramie, wool, silk, glass, metal, activated alumina, activated carbon, silica, zeolites, diatomaceous earth, activated bauxite, fuller's earth, calcium hydroxyappatite, titanates and other materials, or combinations thereof. Combinations of organic and inorganic materials are contemplated and within the scope of the invention. Such membranes may be made using methods known to one of skill in the art.

The Microbiological Interception Enhancing Agent

The nanofibers or membrane that make up the microporous structure are chemically treated with a microbiological interception enhancing agent capable of creating a positive charge on the microbiological interception enhanced filter medium. A cationic metal complex is formed on at least a portion of the surface of at least some of the fibers or the membrane by treating the fibers or membrane with a cationic material. The cationic material may be a small charged molecule or a linear or branched polymer having positively charged atoms along the length of the polymer chain.

If the cationic material is a polymer, the charge density is preferably greater than about 1 charged atom per about every 20 Angstroms, preferably greater than about 1 charged atom per about every 12 Angstroms, and more preferably greater than about 1 charged atom per about every 10 Angstroms of molecular length. The higher the charge density on the cationic material, the higher the concentration of the counter ion associated therewith. A high concentration of an appropriate counter ion can be used to drive the precipitation of a cationic metal complex. The cationic material should consistently provide a highly positively charged surface to the microporous structure as determined by a streaming or zeta potential analyzer, whether in a high or low pH environment. Zeta or streaming potentials of the microporous structure after treatment with a high molecular weight charged polymer can be greater than about +10 millivolts, and often up to about +23 millivolts at a substantially neutral pH.

The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the microporous structure. The cationic material preferably has one or more counter ions associated therewith which, when exposed to a biologically active metal salt solution, cause preferential precipitation of the metal in proximity to the cationic surface to form a cationic metal precipitate.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261, 002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to itself or to the fiber or membrane.

Furthermore, other materials suitable for use as the cationic material include BIOSHIELD® available from Bio-Shield Technologies, Inc., Norcross, Ga. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methlyene-bis-N,N-diglycidylaniline (MBGDA), a crosslinking agent, to covalently bond the PHMB to a polymeric surface. Silver, in the form of silver iodide, is introduced into the network, and is trapped as submicron-sized particles. The combination is an effective biocide, which may be used in the present invention. Depending upon the fiber and membrane material, the MBGDA may or may not crosslink the PHMB to the fiber or the membrane.

The cationic material is exposed to a biologically active metal salt solution such that the cationic metal complex precipitates onto at least a portion of the surface of at least some of the fibers or the membrane. For this purpose, the metals that are biologically active are preferred. Such biologically active metals include, but are not limited to, silver, copper, zinc, cadmium, mercury, antimony, gold, aluminum, platinum, palladium, and combinations thereof. Most preferred are silver and copper. The biologically active metal salt solution is preferably selected such that the metal and the counter ion of the cationic material are substantially insoluble in an aqueous environment to drive precipitation of the cationic metal complex.

A particularly useful microbiological interception enhancing agent is a cationic silver-amine-halide complex. The cationic amine is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT® 100. The chloride counter ion may be replaced with a bromide or iodide counter ion. When contacted with a silver nitrate solution, the silver-amine halide complex precipitates on at least a portion of the fibers or membrane of the microporous structure of the filter medium.

The pH of the surrounding solution does affect the zeta potential of the microbiological interception enhanced filter medium of the present invention. An acidic pH will increase the charge on the filter medium while a basic pH will decrease the charge on the filter medium. Under pH conditions typically encountered in potable water, the microbiological interception enhanced filter medium does retain a minimum positive charge and only at very high pH values does the charge decline below zero millivolts. Exposure to NOM, such as polyanionic acids, will decrease the zeta potential of the microbiological interception enhanced filter medium. This will diminish its microbiological interception capabilities. Therefore, in applications where high levels of NOM are present, an adsorbent prefilter capable of removing the NOM extends the useful life of the microbiological interception enhanced filter medium.

Methods of Making the Microbiological Interception Enhanced Filter Medium

The microbiological interception enhanced filter medium may be made in accordance with processes known to one of skill in the art. Dry laid processes include spun bonding, electrospinning, spinning islands-in-sea processes, fibrillated films, melt blowing, and other dry laid processes known to one of skill in the art. An exemplary dry laid process starts with staple fibers, which can be separated by carding into individual fibers and are then laid together to a desired thickness by an aerodynamic or hydrodynamic process to form an unbonded fiber sheet. The unbonded fibers can then be subjected to hydraulic jets to both fibrillate and hydroentangle the fibers. A similar process can be performed on certain plastic films that when exposed to high pressure jets of water, are converted into webs of fibrillated fibers.

In a preferred wet laid process, a fiber tow is chopped to a specific length, usually in the range of about 1 millimeter to about 8 millimeters, and in particular in the range of about 3 millimeters to about 4 millimeters. The chopped fibers are fibrillated in a device having characteristics similar to a blender, or on a large scale, in machines commonly referred to as a "hi-low", a "beater" or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation. If the surface area is very high, then very little water will be drained from the pulp in a given amount of time and the CSF value will become progressively lower as the fibers fibrillate more extensively. The fibrillated fiber of a given CSF value can be directly used for producing paper or dewatered on a variety of different devices, including a dewatering press or belt, to produce a dewatered pulp. The dewatered pulp can be subsequently used to make a wet-laid paper. Generally, for application in the present invention, a pulp with a CSF of below 100 is used, and preferably, the CSF should be less than or equal to about 45.

The pulp is treated with a cationic material in such a manner as to allow the cationic material to coat at least a portion of the surface of at least some of the fibers thereby imparting a charge on the fibers. Methods of applying the cationic material to the fibers are known in the art and include, but are not limited to, spray, dip, or submergence coating to cause adsorption, chemical reaction or crosslinking of the cationic material to the surface of the fibers. The treated pulp is then rinsed in reverse osmosis/deionized (RO/DI) water, partially dewatered, usually under vacuum, to produce a wet lap that can then be exposed to a biologically active metal salt solution. The use of nearly ion-free rinse water causes the counter-ions associated with the cationic material to be drawn tightly against the treated fiber surface and to eliminate unwanted ions that may cause uncontrolled precipitation of the biologically active metal into sites remote from the cationic surface.

The metal salt solution is infiltrated into the fibers to allow precipitation of the cationic metal complex on a surface of at least a portion of the fibers. The precipitation accurately deposits a metal colloid adjacent to the cationic coating because the counter-ion associated with this coating reacts with the applied metal salt to form colloidal particles. After sufficient exposure to the biologically active metal salt solution, the fibers can be rinsed and excess water is removed. Alternatively, the fibers can be directly sent to pulp preparation systems to create a furnish suitable for paper making.

When silver nitrate is used as the metal salt solution, the presence of precipitated silver can be confirmed by using a Kratos EDX-700/800 X-ray fluorescence spectrometer available from Kratos Analytical, a Shimadzu Group Company, Japan.

The microbiological interception enhanced filter medium comprising a membrane may be made in accordance with processes known to one of skill in the art. Raw material for the membrane may be treated prior to forming the membrane or the cationic material may be applied to the membrane material using known methods in the art and similar to those used to treat the fiber surfaces.

Additives

The strength of the wet laid fiber sheet, especially when wet, may be improved with the addition of various additives. It is well known in the art that the addition of epoxy or acrylic or other resins to the paper making process can provide enhanced wet strength, but these water-dispersed resins often cause lower permeability to the final product, especially as fiber size becomes very small. Although these resins and resin systems can be used in the current invention, it is preferable to use thermoplastic or thermoset materials known in the art, and in either powder, particulate or fiber form.

Useful binder materials include, but are not limited to, polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like. Other potentially applicable materials include polymers such as polystyrenes and acrylonitrile-styrene copolymers, styrene-butadiene copolymers, and other non-crystalline or amorphous polymers and structures.

A more detailed list of binder materials that may be useful in the present invention include end-capped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(11-aminoundecanoic acid); polyaramides, such as poly(imino-1,3-phenyleneiminoisophthaloyl) or poly(m-phenylene isophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenyl-eneisopropylide ne-1,4-phenylene), and poly(sulfonyl-1,4-phenylene-oxy-1,4-phenylenesulfonyl4,4'-biphenylene); polycarbonates, such as poly-(bisphenol A) or poly(carbonyldioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxyterephthaloyl); polyaryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that may be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

A range of binder fibers, including polyethylene, polypropylene, acrylic, or polyester-polypropylene or polypropylene-polyethylene bi-component fibers, or others can be used. Certain types of treated polyethylene fibers, when properly treated, as described below, are optimal, and have the additional benefit of not significantly interfering with the hydrophilic nature of the resulting filter medium when used in modest volumes. Preferred fiber binder materials may include FYBREL® synthetic fibers and/or SHORT STUFF® EST-8, both of which are polyolefin based. FYBREL® is a polyolefin based synthetic pulp that is a highly fibrillated fiber and is commercially available from Mitsui Chemical Company, Japan. FYBREL® has excellent thermal moldability and provides a smooth surface to the filter medium. SHORT STUFF® EST-8 is commercially available from MiniFibers, Inc., Pittsburgh, Pa., and is a highly fibrillated, high density polyethylene.

Preferably, the binder material is present in an amount of about 1% to about 10% by weight, more preferably about 3% to about 6%, and most preferably about 5%. It is preferable that the binder material have a softening point that is significantly lower than a softening point of the nanofiber material so that the filter medium can be heated to activate the binder material, while the microporous structure does not melt and thereby lose porosity.

One or more additives either in a particulate, fiber, whisker, or powder form may also be mixed with the nanofibers or incorporated into the membrane to aid in adsorption of other contaminants or participate in the formation of the microporous structure and interception of microbiological contaminants. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, other adsorbent materials such as super adsorbent polymers (SAPs), or combinations thereof. The additives can also be chemically treated to impart microbiological interception capabilities depending upon the particular application. Such additives are preferably present in a sufficient amount such that the fluid flow in the resultant filter medium is not substantially impeded when used in filtration applications. The amount of additives is dependent upon the particular use of the filtration system.

Exemplary of a wet laid process includes mixing a pulp of 45 CSF fibrillated lyocell fibers with 5% EST-8 binder fibers and dispersing the pulp and binder fibers in deionized water with mixing in a blender to form a furnish with about 1% to about 2% consistency. To this mixture is added about 3% by weight of MERQUAT® 100, which is briefly dispersed into the dilute pulp furnish. The cationic material remains in contact with the pulp for about 4 to about 12 hours until a significant portion has been adsorbed onto at least a portion of the fibers to impart and maintain a positive zeta potential on the fibers. Within about eight hours at room temperature, sufficient MERQUAT® is adsorbed to provide a positive zeta potential on the fibers that is greater than about +10 millivolts. Next, this pulp is partially dewatered under vacuum and rinsed with deionized water to form a wet lap. A metal salt solution, such as, for example, silver nitrate, in an amount equal to 0.5% by weight of the dry nanofibers, is prepared with deionized water, and uniformly poured over the sheet and allowed to stand for a short time to allow precipitation of the biologically active metal with at least a portion of the counter ion associated with the cationic material. Thereafter, the fibers can be directly used in the production of wet laid filter medium.

Filtration Systems Utilizing the Microbiological Interception Enhanced Filter Medium Many types of filtration systems incorporating the current filter medium can be imagined. Described below are certain specific embodiments. However, these filtration systems are exemplary and should not be construed as restricting the scope of the invention.

Precoat Filtration Systems Including Microbiological Interception Enhanced Nanofiber One filtration system of the present invention that utilizes nanofibers treated with the microbiological interception enhancing agent, is an industrial, commercial or municipal filter that uses a precoat applied to a porous septa. This coating is produced by dispersing particles such as diatomaceous earth, perlite or fibers as a precoat applied to the porous septa for filtering liquids such as beer, wine, juices, and other liquids used in the food service or pharmaceutical industry. As the liquid contacts the filter cake, unwanted contaminants are removed while also clarifying the liquid. The charged nanofibers not only remove negatively charged contaminants in the liquid much smaller than the pores of the precoat but greatly improve the mechanical interception of all particles. The nanofibers may be used in conjunction with traditional precoat ingredients such as diatomaceous earth.

Only a small amount of nanofibers are needed in the precoat, generally about 1.5% to about 10% by weight, to produce a significant effect. Preferably, a hydrophilic microbiological interception enhanced filter medium is used in these applications.

Filtration Systems Involving Multiple Layers of Filter Medium

A microbiological interception enhanced filter medium of the present invention can include configurations having more than one layer of the microbiological interception enhanced filter medium. A first microbiological interception enhanced filter medium layer may be positively charged while a second layer may be negatively charged. The negatively charged material can be produced by contacting the nanofibers pulp with a negatively charged compound or material such as a polycarboxylic acid mixed with a small quantity of a crosslinking agent such as a glycerine. Heating the nanofibers after soaking in such a mixture results in the formation of a coating on the nanofibers of negatively charged carboxylic acid polymer crosslinked by the glycerine. The multi-layer microbiological interception enhanced filtration system is capable of intercepting both positively and negatively charged microbiological targets. Again, in applications where NOM is present, an adsorbent prefilter may be needed to preserve the charge on the microbiological interception enhanced filter medium.

Filtration Systems with an Adsorbent Prefilter Combined with the Microbiological Interception Enhanced Filter Medium A microporous filter medium of the present invention treated with the microbiological interception enhancing agent may be used as a flat sheet medium, a pleated medium, or as a spiral wound medium depending upon the application and the filter housing design. It may be used for just about any type of fluid filtration including water and air.

However, the microbiological interception enhanced filter medium may be less effective in the presence of moderate to high levels of NOM such as polyanionic humic acid and fulvic acid, due to the decrease and eventual loss of positive charge on the filter medium in the presence of such acids. Therefore, such applications utilizing the microbiological interception enhanced filter medium alone should be substantially free of or have low levels of polyanionic acids.

In filtration systems containing the microbiological interception enhanced filter medium that may come in contact with fluids that contain NOM, it is prudent to use an adsorbent prefilter to remove the NOM in the influent prior to it contacting the microbiological interception enhanced filter medium. Alternatively, the positively charged filter medium can be formed into a multitude of layers either as a stack of sheets or by conversion into a structure. Under this type of arrangement, the outer layers of the filter medium can be sacrificed to remove the NOM, while the inner layers are protected and provide long-term reduction of microbiological contaminants. Additives that adsorb or absorb NOM may be incorporated into the microporous structure, including anion exchange resins. To avoid this costly loss of sacrificial material, the following examples describe other alternative methods for arranging the protection of the filter medium from the effects of NOM.

1. A Flat Adsorbent Filter Medium as a Prefilter

The microbiological interception enhanced filter medium may be used in conjunction with adsorbent filtration media that serve to intercept NOM interferences prior to their contact with the charged microbiological interception enhanced filter medium. The microbiological interception enhanced filter medium and one or more layers of an adsorbent filtration medium may be used as a flat sheet composite, spiral wound together, or pleated together. Such an adsorbent filtration medium may be manufactured according to U.S. Pat. Nos. 5,792,513 and 6,077,588, as well as other processes in the prior art. A particularly suitable flat sheet adsorbent filtration medium is commercially available as PLEKX® from KX Industries, L.P., Orange, Conn. The flat sheet filtration medium may contain hydrophilic or hydrophobic particles that can also be treated with the microbiological interception enhancing agent, although not necessary, and immobilized on a substrate to provide added microbiological interception capabilities in addition to that provided by the microbiological interception enhanced filter medium. At least one adsorbent layer is preferably placed upstream from the microbiological interception enhanced filter medium to reduce the deleterious effects of NOM on the microbiological interception enhanced filter medium. The microbiological interception enhanced filter medium can serve as one of the substrates used to support the adsorbent used to filter NOM from the influent fluid. For example, the upper layer of the PLEKX® structure can be a particulate prefilter. The core of the PLEKX® composite can be primarily composed of an adsorbent with a high affinity for NOM, and the lower, downstream layer can be the microbiological interception enhanced filter medium. The layers can be bonded into a single cohesive composite structure using the PLEKX® process described in the above-mentioned patents. The result is a high dirt capacity filter structure that provides chemical, particulate, and microbiological interception in a single material. The core of the PLEKX® structure can include a wide range of ingredients useful for the adsorption of chemical contaminants.

2. GAC Filter Medium as an Adsorbent Prefilter

The microbiological interception enhanced filter medium may also be used in conjunction with a bed of granular adsorbent such as, for example, a granular activated carbon (GAC) bed. The granular bed filter should be placed upstream from the microbiological interception enhanced filter medium to remove any charge-reducing contaminants, such as NOM, from the influent prior to contacting the charged microporous filter medium.

3. Solid Composite Block Filter Medium as an Adsorbent Prefilter

The microbiological interception enhanced filter medium may also be used in conjunction with a solid composite block filter medium, preferably comprising activated carbon, placed upstream from the microbiological interception enhanced filter medium to remove any charge-reducing contaminants, such as NOM, from the influent prior to contact with the microbiological interception enhanced filter medium. The activated carbon block may include, but is not limited to, such materials as activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, and combinations thereof to provide additional reduction of contaminants such as heavy metals, arsenic, chlorine, and to improve taste and odor. These materials, as well as the activated carbon, may be treated with the microbiological interception enhancing agent prior to being converted into a solid composite by extrusion, compression molding or other processes known to one of skill in the art. Exemplary processes are described in U.S. Pat. Nos. 5,019,311, and 5,189,092. The solid composite block can contain an anion-exchange resin that is specifically selected for its high capacity to adsorb NOM.

Complete Filtration Devices Combining Adsorbent Prefilters and Microbiological Interception Enhanced Filter Medium One particular embodiment of a filtration system of the present invention includes a composite filter medium, as described above, including the microbiological interception enhanced filter medium and the adsorbent filtration medium. This device is designated to operate as a gravity flow device with a driving pressure of only a few inches water column to a maximum of a few feet of water column. The composite filter medium is forced to first pass through the adsorbent prefilter and then the microbiological interception layer. As shown in FIG. 1, an exemplary filter design incorporates the composite filter medium of the present invention in a filter housing 10 having a clam shell type enclosure. Filter housing 10 has a top portion 12 having an inlet 14, and a bottom portion 16 having an outlet 18. Residing within a sealed cavity defined by the top portion and bottom portion is the composite filter medium 20 shown more accurately in the cross sectional view of FIG. 2. Top portion 12 and bottom portion 16 may be formed from a single sheet of a polymeric material and folded over to provide a clam shell configuration.

Figure 2:
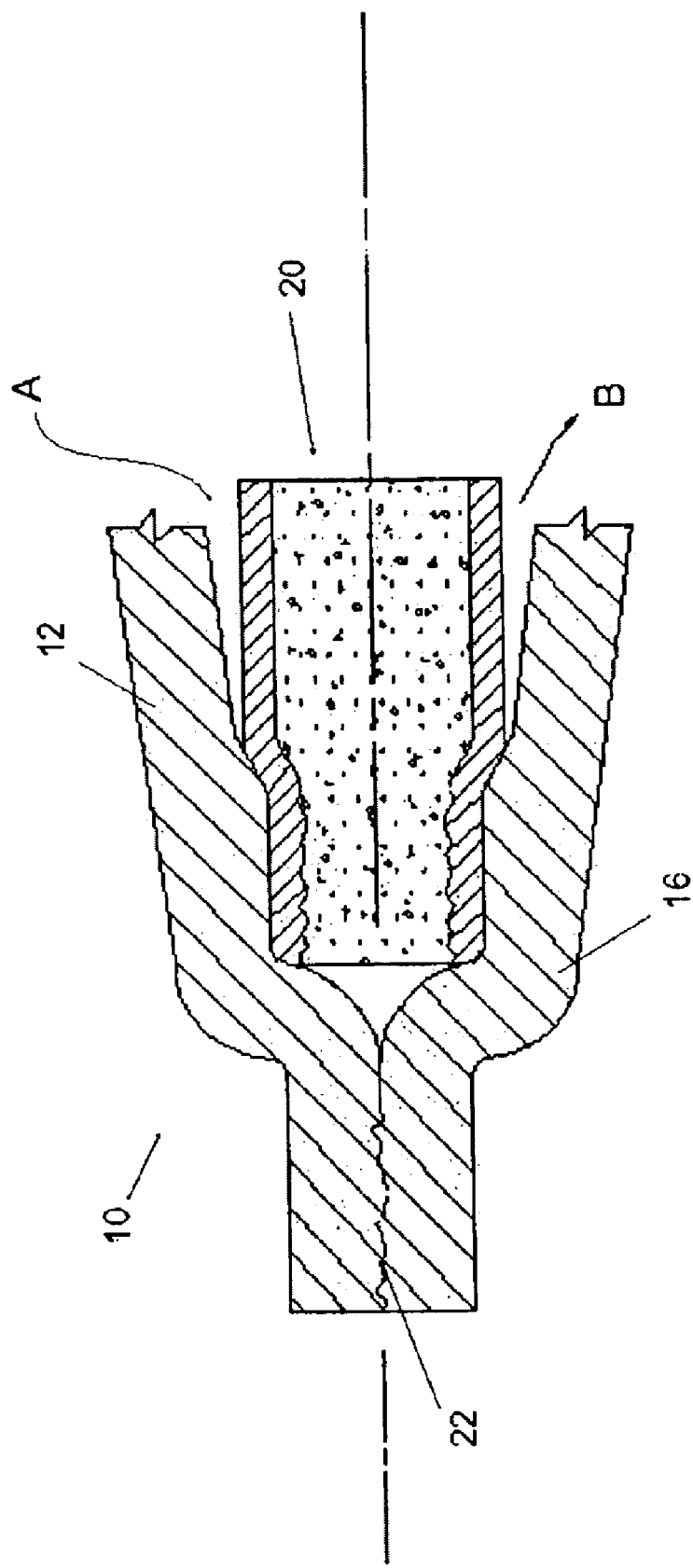
FIG. 2 is a cross sectional view of the filter of FIG. 1 taken at lines 2—2.

To assemble the filter, composite filter medium 20 is cut into substantially the size and shape of the clam shell enclosure. Composite filter medium 20 is secured into bottom portion 16 and top portion 12 is placed over bottom portion 16 and compressed together. The top and bottom shell portions 12, 16 may be welded together creating a weldment 22 around the entire periphery of filter medium 20. As illustrated in FIG. 2, there is shown a substantially impermeable interface between the top and bottom portions and the composite filter medium in the region directly adjacent weldment 22. Excess material on the clam shell enclosure and composite filter medium is simply cut off. It will be understood that other methods of sealing the filter medium within the filter housing may be used such as, but not limited to, adhesives, mechanical clamps, and the like. Although the filter design has a clam shell enclosure, the filter design is not limited to such. Any enclosure that may be sealed such that an influent will not bypass the filter medium would be suitable.

In referring back to FIG. 2, the seal formed between composite filter medium 20 and top portion 12 and bottom portion 16 is such that water being filtered is forced to follow the path illustrated by arrows A and B, and cannot bypass composite filter medium 20. In fact, at the periphery of composite filter medium 20, the pressure exerted by the seal increases the density of the filter medium so that contact time of the water being filtered with composite filter medium 20 in this peripheral region is increased and filtration efficiency enhanced.

During production of the filter, assurances concerning the seal and assembly integrity may be obtained using a vision system, and gas or aerosol pulse testing. The gas or aerosol pulse test uses a tiny pulse of dilute butane or fog-oil smoke that is entirely adsorbed or intercepted by an intact filter, but will significantly penetrate a defective filter. Other off-line test procedures known to one of skill in the art may be used to methodically examine the quality of the seal between the filter medium and the enclosure.

The wall of the filter housing may be sufficiently thin and flexible so that when the filter is contacted with water, the modest pressure produced by the hydrostatic load of the incoming water causes top portion 12 and bottom portion 16 to bow away slightly from and provide a clearance space between the inner surface of top portion 12 and bottom portion 16, and composite filter medium 20. This clearance space assists in distributing the water across the influent surface of composite filter medium 20 and provides drainage of the effluent into outlet 18.

Figure 3:
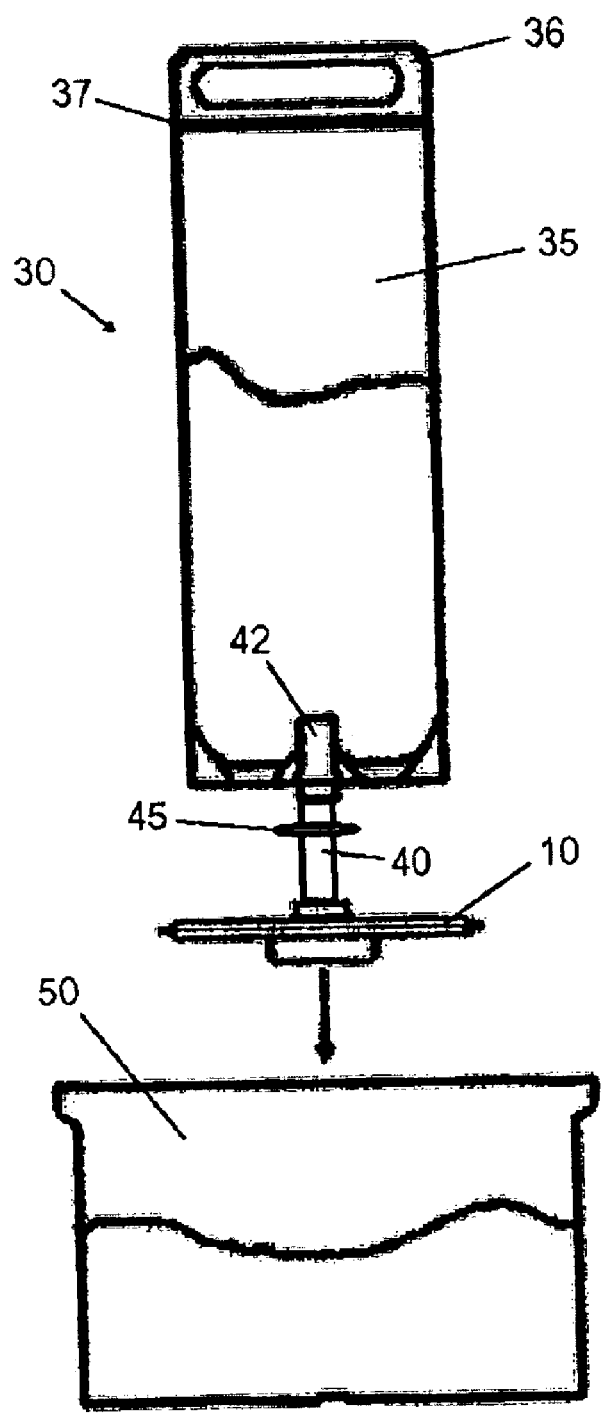
FIG. 3 is a front plan view of an exemplary gravity flow filtration system of the present invention.

Referring to FIG. 3, there is shown a front plan view of a filtration system 30 of the present invention useful in providing potable water in a gravity flow device that may be useful in developing countries where safe, potable water of suitable microbiological quality is scarce. Although water is discussed as the liquid influent, it is within the scope of the invention to contemplate the filtration of other liquids. Filtration system 30 has a first reservoir 35 that is a raw water collection transport container. First reservoir 35 may be a bag configuration as shown constructed of a substantially leak proof material such as a polymeric material, i.e., polyester, nylon, a polyolefin such as polyethylene, polyvinyl chloride, and multi-layer films of the like. For ease of use, first reservoir 35 may have a reinforced opening and a handle 36 for carrying and hanging first reservoir 35 to provide a pressure head during filtration. Preferably, first reservoir 35 has a resealable opening 37 that when closed provides a substantially water-tight seal. Such resealable openings are known to one of skill in the art or may include a threaded opening with a screw-on cap.

First reservoir 35 is preferably equipped with an output hose 40 such that water stored in the reservoir may be drained for filtration and eventual use. Output hose 40 is preferably made with a food-safe grade of flexible polymer. Output hose 40 may be opened and closed using a simple clamp. Output hose 40 may be permanently attached to first reservoir 35 by ultrasonic welding or retained simply by friction. Output hose 40 preferably has an internal extension end 42 within first reservoir 35 such that internal extension end 42 extends above the bottom of the first reservoir 35 to provide an area for capturing sediment that can settle prior to water filtration. By limiting the amount of sediment present in the influent prior to water filtration, the useful life of the filtration system is prolonged.

Output hose 40 connects first reservoir 35 to a filter 10, described above, including the composite filter medium of the present invention. A clamp 45 may be fitted on output hose 40 at any point along the length of output hose 40. Such clamps are well known in the art and may be a simple one piece configuration made of a flexible polymer or metal. When the clamp is in an open position, water from first reservoir 35 flows freely into filter 10. Filter 10 is removably connected to output hose 40. The outlet of filter 10 is then connected to a second reservoir 50. Second reservoir 50 serves as a collection vessel for the filtered water or effluent. Alternatively, filter 10 and second reservoir 50 may be connected together via a second output hose (not shown). Second reservoir 50 generally is equipped with a means for dispensing the filtered water.

The above filtration system may be used as follows. A user takes first reservoir 35, with or without output hose 40 attached thereto, to a water source. If output hose 40 is still attached to first reservoir 35, clamp 45 must be in a closed position or first reservoir 35 must be sealed by other means. First reservoir 35 is filled with a quantity of raw water and its opening again sealed while the user carries first reservoir 35 back to a preferred location such as a residence. It is possible that the raw water is contaminated with microorganisms and chemical contaminants and may not be potable. To facilitate filtration, first reservoir 35 is suspended or hung from a support means. Depending upon any significant sediment present as evidenced by turbidity, the raw water is allowed to remain suspended for a period of time sufficient for the sediment to settle below the height of internal extension end 42 of output hose 40 within first reservoir 35. Of course, should the water be relatively clear, there is no need to suspend first reservoir 35 for such a period of time. Output hose 40 is attached to first reservoir 35, if previously detached, and secured to filter 10. Filter 10 is secured to second reservoir 50 for collecting the filtered water. Clamp 45 is then placed in an open position and the water is allowed to flow into filter 10 wherein the water once treated through composite filter medium 20, is rendered potable, and collected in second reservoir 50. To preserve the potability of the filtered water, the surfaces of second reservoir 50 may be made from or treated with a disinfectant or with the microbiological interception enhancing agent. Preferably, the disinfectant used would not alter or affect the taste of the water.

Typical water flow rates are about 25 to about 100 ml/minute for a device equipped with a filter of about 3"×5" size and operated at about 6" water column pressure. This provides one liter of potable water in about 10 to 40 minutes having at least about 6 log reduction in bacteria and at least about 4 log reduction in viral contaminants. Continual use of filter 10 will likely develop, by progressive deposition thereon, a layer of particles that will slow the flow rate until the filtration process takes an unacceptable amount of time. Although the flow rate is diminished, the filter will maintain its microbiological interception capabilities for an extended period.

Figure 4:
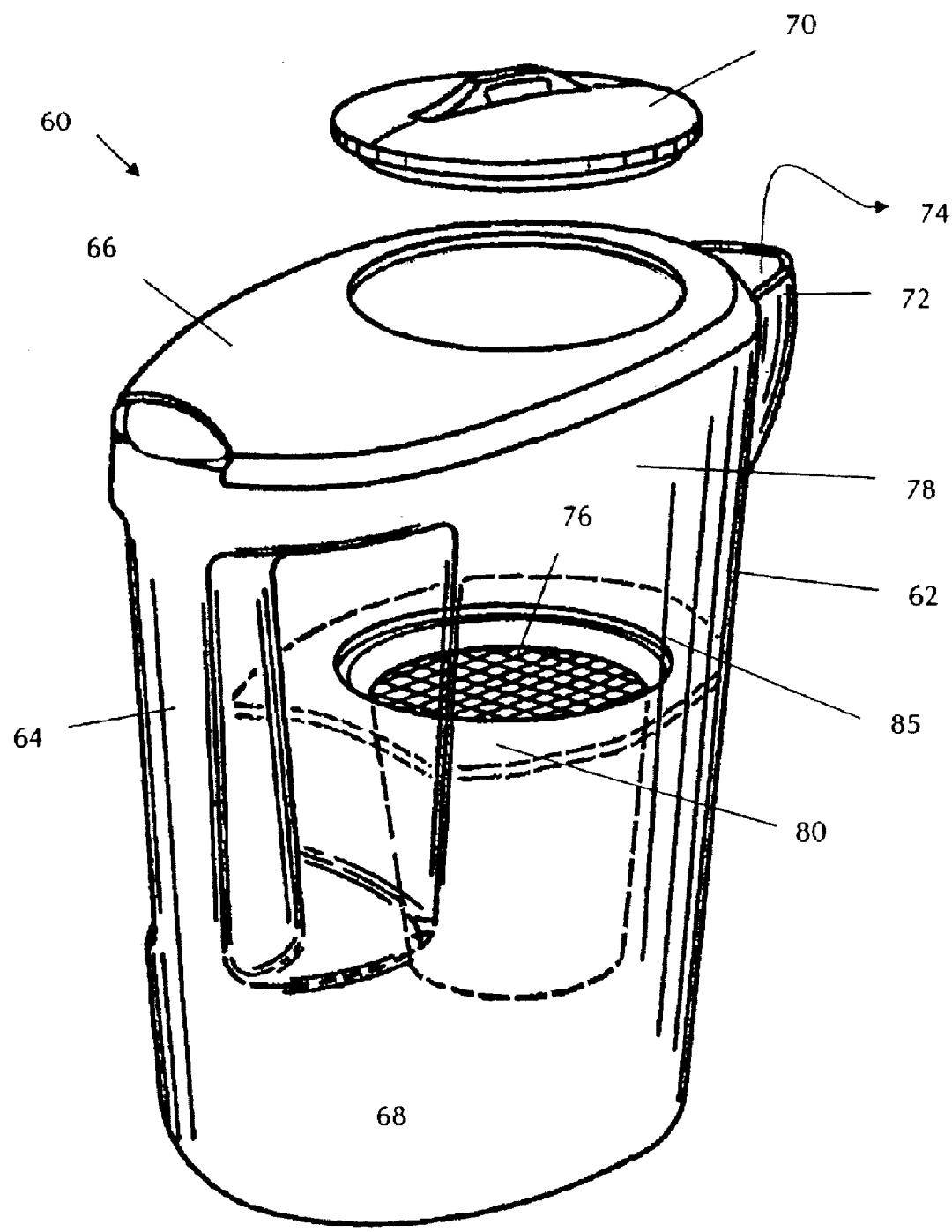
FIG. 4 is a perspective view of another exemplary gravity flow filtration system of the present invention.

Another gravity flow device incorporating a filter medium of the present invention includes an exemplary carafe design as illustrated in FIG. 4 for filtering, storing and dispensing filtered water or other fluids. Although the carafe shown is primarily round, the carafe 60 may assume any shape depending upon its use and environment, and is a matter of design choice. A basic carafe has a housing 62 with a handle 64 and cover 66. Carafe 60 is divided into a lower reservoir or storage chamber 68 and an upper reservoir 78 that are enclosed by lid 70 and cover 66 located within housing 62. Spout 72 facilitates the removal of filtered water through outlet 74 of storage chamber 68.

Upper reservoir 78 and storage chamber 68 are separated by partition 80 that is provided with a filter receiving receptacle 85 having an opening (not shown) in the bottom thereof. In one embodiment, a flat composite filter medium 76 of the present invention is placed into filter receiving receptacle 85 with a water tight seal to segregate upper reservoir 78 and storage chamber 68. Placement of filter medium 76 into filter receptacle 85 may be accomplished using means known to one of skill in the art including, but not limited to, a snap or hinged mechanism. Filter medium 76 is preferably manufactured as a replaceable cartridge. Other features of the carafe design may be incorporated into the present invention without departing from the scope of the invention. The filter medium may comprise any microporous structure having a mean flow path of less than about 1 micron and so treated as to provide at least about 4 log reduction of microbiological contaminants smaller than the mean flow path of the filter medium. Preferably, the filter medium has a volume of less than about 500 cm$^3$ and has an initial flow rate of greater than about 25 ml/minute.

A user would pour raw water into upper reservoir 78 and allow the raw water to pass through filter medium 76 under the influence of gravity. Filtered water is collected in storage chamber 68. As the raw water passes through the filter medium of the present invention with sufficient contact time, the filter medium renders the water potable by providing a high titer reduction of microorganisms. The log reduction value (LRV) of microorganisms is dependent upon the contact time of the filter medium with the flowing water. To provide about 8 log reduction value of microorganisms, the required contact time is about 6 to about 10 seconds.

Carafe 60 may also have an indicator (not shown) that allows a user to keep track of the age of the filter to gauge when the useful life of the filter medium has been expended. Other types of indicators may also be used such as an indicator for indicating the number of refills of carafe 60, for measuring the volume of water or liquid that passes through the filter medium, and the like.

Other Filtration Systems

A filter medium of the present invention, in particular, the composite filter medium, may also be incorporated into a point-of-use application such as a sports bottle design for use as a personal water filtration system operating under a slight pressure, about 1 psi. A suitable sports bottle design is disclosed in International Patent Application No. WO 01/23306 wherein the filter medium may be incorporated into the filter receptacle of the sports bottle.

For other point-of-use applications, the microbiological interception enhanced filter medium of the present invention may further be incorporated into end-of-tap (EOT), under-sink, counter-top, or other common consumer or industrial filtration systems and configurations for use in pressurized systems. The filter system may include a prefilter comprising a bed of adsorbent particles or a solid adsorbent composite block. The microbiological interception enhanced filter medium can be a pleated or a spiral wound construction, or formed into a thick mat by vacuum formation on a suitable mandrel to create a wet-formed or dry-formed cartridge.

EXAMPLES

The following examples are provided to illustrate the present invention and should not be construed as limiting the scope of the invention.

Porometry studies were performed with an Automated Capillary Flow Porometer available from Porous Materials, Inc., Ithaca, N.Y. Parameters determined, using standard procedures published by the equipment manufacturer, include mean flow pore size and gas (air) permeability. The flow of air was assayed at variable pressure on both the dry and wet filter medium. Prior to wet runs, the filter medium was initially immersed in silicon oil for at least 10 minutes while held under high vacuum.

Zeta or streaming potential of various filter media was determined using streaming potential and streaming current measured with a BI-EKA Electro-Kinetic Analyzer available from Brookhaven Instruments, of Holtsville, N. Y. This instrument includes an analyzer, a flat-sheet measuring cell, electrodes, and a data control system. The analyzer includes a pump to produce the pressure required to pass an electrolyte solution, generally 0.0015M potassium chloride, from a reservoir, through the measuring cell containing a sample of the filter medium described herein. Sensors for measuring temperature, pressure drop, conductivity and pH are disposed externally of the cell. In accordance with this method the electrolyte solution is pumped through the porous material. As the electrolyte solution passes through the sample, a displacement of charge occurs. The resulting "streaming potential and/or streaming current" can be detected by means of the electrodes, placed at each end of the sample. The zeta (streaming) potential of the sample is then determined by a calculation according to the method of Fairbrother and Mastin that takes into account the conductivity of the electrolyte.

Bacterial challenges of the filter media were performed using suspensions of *Escherichia coli* of the American Type Culture Collection (ATCC) No. 11775 to evaluate the response to a bacterial challenge. The response to viral challenges was evaluated using MS-2 bacteriophage ATCC No. 15597-B1. The Standard Operating Procedures of the ATCC were used for propagation of the bacterium and bacteriophage, and standard microbiological procedures, as well known in the art, were used for preparing and quantifying the microorganisms in both the influent and effluent of filters challenged with suspensions of the microbiological particles.

Examples 1–3

Filter Medium Made with Untreated Lyocell Fibers (Comparative)

Filter medium made from untreated lyocell fibers having a mean flow path of about 0.3 to about 0.6 microns were prepared in accordance with the following method.

Dry EST-8 binder fibers having a weight of 0.45 g, commercially available from MiniFibers, Inc., was fully dispersed in 1.0 L of deionized water in a kitchen style blender on a pulse setting. Fibrillated lyocell fibers with a Canadian Standard Freeness of 45 and having a dry weight of 120.0 g were added as wet pulp to the dispersed binder fibers. The dispersed fiber mixture was blended for another 15 seconds. The fiber mixture was poured into a larger industrial Waring blender with an additional 1.0 L of deionized water and blended for an additional 15 to 30 seconds. The fiber mixture was poured into a 30.5×30.5 cm$^2$ stainless steel FORMAX® paper deckle filled with about 12.0 L of deionized water and fitted with a 100 mesh forming screen. A 30×30 cm$^2$ stainless steel agitator plate having 60 holes of 2 cm in diameter was used to plunge the fiber mixture up and down from top to bottom about 8 to 10 times. The water was removed from the fiber mixture by pulling a slight vacuum below the deckle to cause the fibers to form on the wire. Once the bulk of the water is removed, supplemental dewatering is accomplished with a vacuum pump to remove additional excess moisture and to create a relatively smooth, flat, fairly thin paper-like sheet. The resulting sheet is separated from the screen and combined with a blotter sheet on both top and bottom. The combination of sheets is gently rolled with a 2.27 kg marble rolling pin to remove excess water and smooth out the top surface of the sheet. The sheet is then placed between two fresh and dry blotter sheets and placed on a FORMAX® sheet dryer for about 10 to about 15 minutes at about 120° C. The dried filter medium is separated from the blotter sheets and directly heated on the FORMAX® sheet dryer for about 5 minutes on each side to activate the dry binder fibers.

Table I shows the porometry and air permeability test results performed on filter medium made from untreated lyocell fibers of varying thicknesses made using the above process.

TABLE I

Mean Flow Path and Porometry of Filter Medium Made With Untreated Lyocell Fibers

| Example # | Sample Thickness (mm) | Mean Flow Path ($\mu$m) | Gas Permeability (L/cm$^2$ at 1 psi) |
|---|---|---|---|
| 1 | 0.45 | 0.3804 | 5.48 |
| 2 | 0.66 | 0.6708 | 4.50 |
| 3 | 0.63 | 0.4316 | 5.30 |

The resulting filter medium made with untreated lyocell fibers had a reproducible streaming potential of about −9.0 millivolts.

Example 4

Filter Medium Made with Lyocell Fibers Treated with the Microbiological Interception Enhancing Agent To a blender were added 12.0 g dry weight lyocell fibers as a 10% by weight wet pulp having a Canadian Standard Freeness of about 45, 0.45 g SHORT STUFF® EST-8 binder fibers, and 1.0 L deionized water. The mixture was blended until the fibers were fully dispersed. To the blender was added 3.0 ml of MERQUAT® 100 as a 30% aqueous solution and the fibers blended with the MERQUAT® 100 for about 10 seconds and left to stand for at least about 6 hours. After about 6 hours, the fibers were poured into a standard 8 inch Brit jar fitted with a 100 mesh forming wire and excess water removed under vacuum. The resulting pulp sheet was rinsed with 500 ml of deionized water. The excess water was again removed by vacuum.

A dilute silver nitrate solution was poured uniformly over the pulp sheet to provide full exposure and saturation, providing about 0.1425 g of silver per sheet. The silver nitrate solution was left on the pulp sheet for at least about 15 minutes and excess water removed under vacuum pressure. The silver-treated pulp sheet was then torn into small pieces and placed in a WARING® blender and re-dispersed in 2.0 L of deionized water. A second 3.0 ml portion of the MERQUAT® 100 solution was added to the dispersion and the mixture blended for about 10 minutes and the contents poured into a 30.5×30.5 cm$^2$ stainless steel FORMAX® paper deckle fitted with a 100 mesh forming screen. Paper-like sheets of the microbiological interception enhanced filter medium were made in the same manner as the untreated lyocell filter media described in Examples 1 to 3.

The zeta potential of the filter medium was consistently greater than about +10 millivolts at a pH of about 7.0.

Examples 5–23

Comparison of Microbiological Interception with the Microbiological Interception Enhanced Filter Medium of the Present Invention and the Untreated Lyocell Filter Medium Sheets of fibrillated lyocell filter medium either untreated or treated with MERQUAT® 100 and silver, as described in Examples 1 to 4, were folded twice and cut into standard cone-shaped funnels and placed into small sterilized glass funnels. Deionized water was used to pre-wet each filter medium. Approximately 125 ml of various microbiological challenges were poured through the filters and the effluents collected in sterile 250 ml Erlenmeyer flasks. The effluents were subjected to serial dilution in duplicate and plated on petri dishes following standard laboratory procedures as required for each organism and left overnight in 37° C. heated incubators. The next day all test results were recorded. Table II summarizes the log reduction values of a series of tests run using microbiological challenges made with de-ionized water.

TABLE II

LRVs of Filter Media Made With Treated And Untreated Fibrillated Lyocell Fibers

| Ex # | E. coli LRV (Treated) | E. coli LRV (Untreated) | Ex # | MS2 LRV (Treated) | MS2 LRV (Untreated) |
|---|---|---|---|---|---|
| 5  | 9.2  | —    | 14 | 7.47 | —    |
| 6  | 9.2  | —    | 15 | 7.47 | —    |
| 7  | 9.2  | —    | 16 | 7.47 | —    |
| 8  | 9.2  | —    | 17 | 7.76 | —    |
| 9  | 9.2  | —    | 18 | 7.76 | —    |
| 10 | 9.2  | —    | 19 | 7.76 | —    |
| 11 | 9.4  | <1.0 | 20 | 8.58 | <1.0 |
| 12 | 7.65 | <1.0 | 21 | 8.58 | <1.0 |
| 13 | 9.98 | <1.0 | 22 | 8.67 | <1.0 |
|    |      |      | 23 | 8.19 | <1.0 |

— = Minimal to no reduction.

As illustrated in Table II, the filter medium made from lyocell fibers treated with MERQUAT® 100 and silver provided significant microbiological interception capabilities as compared to filter medium made from untreated lyocell fibers. The efficacy of the microbiological interception enhanced filter medium when challenged with M52 viral particles illustrates that a filtration system of the present invention would prove effective in removing nano-sized pathogens such as viruses.

Examples 24–27

Microbiological Interception Capability of the Filter Medium Made with Treated Lyocell Fibers in the Presence of Polyanionic Acids As discussed above, NOM such as polyanionic acids reduce the positive zeta potential and, thereby, reduce the efficacy of the microbiological interception enhanced filter medium. After exposure to 500 ml humic acid (0.005 g/1.0 L $H_2O$), the zeta potential of the microbiological interception enhanced filter medium decreased from +14.1 to −14.4. Likewise, after exposure to 500 ml fulvic acid (0.005 g/1.0 L $H_2O$), the zeta potential of the microbiological interception enhanced filter medium decreased from +10.1 to −8.9. Examples 24 to 27 show the reduction in microbiological interception capabilities of the filter medium made with lyocell fibers treated with MERQUAT® 100 and silver in the presence of humic and fulvic acid solutions.

Small discs of the filter medium treated with MERQUAT® 100 and silver were folded and placed in small sterilized glass funnels to form a filter and pre-wetted with de-ionized water. Challenge solutions of E. coli and MS2 viral particles were made with humic acid and fulvic acid, respectively. Approximately 125 ml of the challenge solutions were poured through the filters and the effluent collected in sterile 250 ml Erlenmeyer flasks. The effluent was diluted and plated on petri dishes following standard laboratory procedures. Log reduction values of E. coli and MS2 viral particles are summarized in Tables III and IV below.

TABLE III

LRVs Of The Microbiological Interception Enhanced Filter Media In The Presence Of Fulvic Acid

| Ex # | E. coli (LRV) | MS2 (MRV) |
|---|---|---|
| 24 | 4.68 | 4.23 |

TABLE IV

LRVs Of The Microbiological Interception Enhanced Filter Media In The Presence Of Humic Acid

| Ex # | E. coli (LRV) | MS2 (MRV) |
|---|---|---|
| 25 | 3.78 | 4.23 |
| 26 | 3.02 | 1.64 |
| 27 | 6.73 | 3.58 |

Clearly, the LRVs of the microbiological interception enhanced filter media in the presence of NOM are significantly lower than the 7 to 9 log reduction of E. coli and MS2 absent NOM interference as shown in Table II.

Examples 28–46

Microbiological Interception Capability of the Filter Medium Made with Treated Lyocell Fibers and an Adsorbent Layer in the Presence of Polyanionic Acids In order to decrease the impact of NOM on the filter medium as shown in Examples 24 to 27, an adsorbent prefilter was added to the filter to remove or trap the NOM in the influent prior to contact with the filter medium. The adsorbent layer is PLEKX® made with 600 g/m² of finely ground coal-based activated carbon having a surface area of 1000 m²/g, and is commercially available from KX Industries, L.P.

A composite filter medium combining two (2) layers of a filter medium made with the microbiological interception enhanced filter medium and one (1) PLEKX® layer was fitted in ceramic Buchner funnels over a metal drainage screen. The three (3) layers were secured in each Buchner funnels with a hot melt adhesive to prevent any bypass of the influent. A head pressure of water about 5 cm in depth was maintained in the Buchner funnel at all times. The filters of examples 28 to 34 were charged with sterile deionized water prior to the microbiological challenge and were not exposed to either humic or fulvic acids. Results shown in Table V below show that the efficacy of the composite filter medium with the addition of the adsorbent layer is similar to the results shown in Table II above.

The filters of examples 35 to 40 were charged with 500 ml of a humic acid solution (0.005 g/1 L $H_2O$) prior to the microbiological challenge. Results are shown in Table VI below. The filters of examples 41 to 46 were charged with 500 ml of a fulvic acid solution (0.005 g/1 L $H_2O$) prior to the microbiological challenge. Results are shown in Table VII below.

TABLE V

LRVs Of Filter Media Made With Fibrillated Lyocell Fibers Treated With MERQUAT® 100 And Silver With PLEKX® Absent NOM Interference

| Ex # | E.coli LRV | Ex # | MS2 LRV |
|---|---|---|---|
| 28 | 7.89 | 31 | 8.06 |
| 29 | 7.89 | 32 | 8.06 |
| 30 | 7.89 | 33 | 8.49 |
|    |      | 34 | 8.49 |

TABLE VI

LRVs Of Filter Media Made With Fibrillated Lyocell Fibers
Untreated And Treated with MERQUAT ® 100 And Silver
With PLEKX ® In The Presence Of Humic Acid

| Ex # | E.coli LRV | Ex # | MS2 LRV |
|---|---|---|---|
| 35 | 8.75 | 38 | 8.53 |
| 36 | 8.75 | 39 | 8.53 |
| 37 | 8.75 | 40 | 8.53 |

TABLE VII

LRVs Of Filter Media Made With Fibrillated Lyocell Fibers
Untreated And Treated With MERQUAT ® 100 And Silver
With PLEKX ® In The Presence Of Fulvic Acid

| Ex # | E.coli LRV | Ex # | MS2 LRV |
|---|---|---|---|
| 41 | 8.85 | 44 | 7.77 |
| 42 | 8.85 | 45 | 7.77 |
| 43 | 8.85 | 46 | 7.77 |

The data shows that the use of an adsorbent prefilter such as PLEKX®, placed upstream from the microbiological interception enhanced filter medium, maintained or improved the microbiological interception capabilities of the filter medium by removing the NOM in the influent before the influent contacted the microbiological interception enhanced filter medium. The adsorbent prefilter medium does not need to be treated with the microbiological interception enhancing agent to maintain the efficacy of the microbiological interception enhanced filter medium. It may be a cost saving measure not to treat the adsorbent prefilter medium. Thus, a composite filter medium including the microbiological interception enhanced filter medium and an adsorbent layer positioned upstream from the microbiological interception enhanced filter medium would be robust enough to withstand interference from NOM.

Examples 47–48

E. coli Challenges of a Filtration System of the Present Invention

Two filtration systems of the present invention, as shown in FIG. 3, including a composite filter medium comprising two (2) layers of an adsorbent filter medium, PLEKX® made with 600 g/m² of coal-based activated carbon having a surface area of 1000 m²/g, and a single layer of the microbiological interception enhanced filter medium made from treated fibrillated lyocell fibers as described in Example 4 were assembled using the clam shell filter design of FIGS. 1 and 2 described above. A supporting layer of PLEKX® was placed in the bottom of each filter housing and glued into place using an ethylene-vinyl acetate (EVA) hot melt. The layer of microbiological interception enhanced filter medium was glued to the first PLEKX® layer, followed by a second PLEKX® layer that was also glued into place atop the microbiological interception enhanced filter medium. This configuration uses only one of the PLEKX® layers as an adsorbent prefilter, while the other PLEKX® layer serves primarily as a support for the microbiological interception enhanced filter medium. The outside edges of the housing were also glued and pressed firmly together to prevent any bypass leakage to the outside of the housing. The dimensions of active filter area within the boundary defined by the hot melt material was between 5 cm to 6 cm wide and 8 cm to 10 cm long, providing an active filter area of between 40 cm² and 60 cm². While hot melt was used during this prototype testing, filter assembly using ultrasonic or other welding methods may be applied during commercial production.

A 0.635 cm (0.25 inch) inside diameter hose was attached to the inlet of the filter housing using a plastic fitting and glued securely into place. The outlet of the filter was open to allow fluid to exit the filter housing. The hose attached to the filter inlet was attached to a glass Pyrex funnel to produce a total inlet water column of approximately 30 cm to 60 cm. Test suspensions were poured into the funnel to challenge the filter with various organisms.

Approximately 500 ml of de-ionized water was poured through the filtration system to pre-wet the filter medium inside the housing. For E. coli testing, a hose and funnel with a combined height of 60 cm was used to provide head pressure. The flow rate at this influent pressure was 70 ml/min. A challenge suspension of E. coli was poured through the system and the effluents collected in sterile 250 ml Erlenmeyer flasks. The effluents were subjected to serial dilution in duplicate and plated on petri dishes following standard laboratory procedures and left overnight in 37° C. heated incubators. The next day all test results were recorded and these are listed in Table VIII below.

TABLE VIII

Microbiological Challenges Of A Filtration System
Of The Present Invention With E. coli

| Ex # | No. of E. coli in Challenge | # of colonies forming/plate | LRV |
|---|---|---|---|
| 47 | $8.4 \times 10^8$ | 0 | 8.92 |
| 48 | $8.4 \times 10^8$ | 0 | 8.92 |

Thus, a filtration system of the present invention utilizing a composite filter medium including a PLEKX® prefilter and the microbiological interception enhanced filter medium will provide greater than 8.5 log reduction of E. coli at a flow rate of approximately 1 to 2 ml/minute·cm².

Example 49–51

MS2 Challenges of a Filtration System of the Present Invention

Three filters were constructed in a similar fashion as for the E. coli challenge as described in examples 47 and 48 above, for determining the viral interception capability of a filtration system of the present invention. In two filters, Examples 49 and 50, a layer of netting was installed at the bottom, effluent side, of the filter housing, followed by a layer of the microbiological interception enhanced filter medium, followed by a single top layer of PLEKX® made with 600 g/m² of coal-based activated carbon having a surface area of 1000 m²/g. For the third filter, Example 51, the plastic netting was replaced with a metal 100 mesh screen as the bottom support layer. For the MS2 challenge, a hose and funnel of 30 cm was used to reduce the flow rate and allow for longer contact time through the composite filter medium. Deionized water was poured through the system to pre-wet the layers and verify that the housing had no leaks. A flow rate of 38 ml/ minute was recorded for the 30 cm high water column. After the de-ionized water exited through the system, the MS2 challenge solution was poured through the system. The effluent was collected in sterile Erlenmeyer flasks, diluted and plated on Petri dishes following standard procedures for MS2 and left overnight. The next day all test results were recorded and listed in Table IX below.

TABLE IX

Microbiological Challenges Of The Filter With MS2 Bacteriophage

| Ex # | No. of MS2 in Challenge | # of colonies forming/plate | LRV |
|---|---|---|---|
| 49 | $6.12 \times 10^8$ | 0 | 8.78 |
| 50 | $6.12 \times 10^8$ | 0 | 8.78 |
| 51 | $6.12 \times 10^8$ | 0 | 8.78 |

A filtration system of the present invention utilizing a composite filter medium including a PLEKX® prefilter and the microbiological interception enhanced filter medium is shown to provide greater than 8.5 log reduction of MS2 at a flow rate of approximately 0.75 ml/minute·cm$^2$.

Examples 52 and 53

Long Term MS2 Challenges of a Filtration System of the Present Invention

These examples assess the effectiveness of a filtration system of the present invention when challenged with M52 bacteriophage and having a composite filter medium including two (2) layers of the microbiological interception enhanced filter medium and two (2) layers of PLEKX® as described earlier.

Two filtration systems of the present invention were prepared by securing a 100 mesh screen inside a filter enclosure as shown in FIGS. 1 and 2. Two layers of the microbiological interception enhanced filter medium were placed atop the mesh screen followed by two layers of PLEKX®. Each layer was glued securely in place to prevent bypass. The filter enclosure was sealed with the glue as well. A 0.635 cm (0.25 inch) inner diameter hose was attached securely to the inlet of the filter housing. The outlet of the filter housing was open to allow the passage of fluid. A funnel was securely attached to each filter to provide one with a 25.4 cm (10 inches) water column, and the other filter with a 10.2 cm (4 inches) water column for testing of microbiological challenges.

Deionized water, approximately 500 ml, was passed through each filtration system to pre-wet the filter medium and verify that no bypass was occurring. Subsequently 500 ml of an MS2 challenge, prepared in deionized water, was passed through each system. The effluent was collected in sterile Erlenmeyer flasks, diluted and plated on Petri dishes following standard procedures for the organism and left overnight. After 24 hours, an additional 500 ml of deionized water was passed through the system followed by another 500 ml MS2 challenge. This protocol was continued every 24 hours until the filter media no longer provided an LRV above 4. The results are shown in Tables X and XI below.

TABLE X

Example 52: Efficacy Of A Filtration System Of The Present Invention With A 25.4 cm Water Column

| Total Amount of H$_2$O (L) | Time in Use (hours) | No. of MS2 in Challenge | LRV | Flow Rate (ml/min.) |
|---|---|---|---|---|
| 1.0 | 0 | $2.84 \times 10^8$ | 8.45 | 28 |
| 2.0 | 24 | $4.93 \times 10^8$ | 7.97 | 32 |

TABLE X-continued

Example 52: Efficacy Of A Filtration System Of The Present Invention With A 25.4 cm Water Column

| Total Amount of H$_2$O (L) | Time in Use (hours) | No. of MS2 in Challenge | LRV | Flow Rate (ml/min.) |
|---|---|---|---|---|
| 3.0 | 48 | $4.57 \times 10^8$ | 8.66 | 32 |
| 4.0 | 72 | $4.55 \times 10^8$ | 7.52 | 36 |
| 5.0 | 96 | $1.76 \times 10^9$ | 5.65 | 38 |
| 6.0 | 120 | $1.39 \times 10^9$ | 5.66 | 38 |
| 7.0 | 144 | $1.48 \times 10^9$ | 3.03 | 36 |
| 8.0 | 168 | $1.56 \times 10^9$ | 2.22 | 30 |

TABLE XI

Example 53: Efficacy Of A Filtration System Of The Present Invention With A 10.2 cm Water Column

| Total Amount of H$_2$O (L) | Time in Use (hours) | No. of MS2 in Challenge | LRV | Flow Rate (ml/min.) |
|---|---|---|---|---|
| 1.0 | 0 | $2.05 \times 10^9$ | 9.31 | 12 |
| 2.0 | 24 | $2.16 \times 10^9$ | 9.33 | 15 |
| 3.0 | 48 | $1.46 \times 10^9$ | 9.16 | 15 |
| 4.0 | 72 | $1.05 \times 10^9$ | 9.02 | 17 |
| 5.0 | 96 | $1.52 \times 10^9$ | 9.18 | 16 |
| 6.0 | 120 | $1.31 \times 10^9$ | 9.12 | 13 |
| 7.0 | 144 | $1.19 \times 10^9$ | 9.08 | 13 |
| 8.0 | 168 | $1.32 \times 10^9$ | 8.23 | 13 |
| 9.0 | 192 | $8.67 \times 10^8$ | 8.93 | 16 |
| 10.0 | 216 | $1.34 \times 10^9$ | 9.13 | 10 |
| 11.0 | 240 | $1.10 \times 10^9$ | 9.04 | 11 |
| 12.0 | 264 | $1.24 \times 10^9$ | 7.76 | 9 |
| 13.0 | 288 | $1.24 \times 10^9$ | 8.27 | 9 |
| 14.0 | 316 | $1.02 \times 10^9$ | 3.62 | 7 |
| 15.0 | 340 | $1.04 \times 10^9$ | 3.41 | 8 |
| 16.0 | 364 | $1.03 \times 10^9$ | 3.36 | 10 |
| 17.0 | 388 | $1.07 \times 10^9$ | 3.03 | 10 |

The useful life of the filtration system of Example 52 with a pressure head of 25.4 cm provided an acceptable MS2 log reduction for 6.0 L of water for 120 hours. However, when the pressure head was 10.2 cm, as in Example 53, the useful life of the filtration systems was extended, providing acceptable log reduction values of MS2 for a volume of 13.0 L of water and 364 hours. It is apparent that the flow rate will affect the microbiological interception capabilities of the filtration system. From the results of Examples 52 and 53, a lower flow rate will provide more effective microbiological interception due to greater contact time of the microorganisms with the filter medium.

Example 54

Long Term *E. coli* Challenges of a Filtration System of the Present Invention

This example assesses the effectiveness of a filtration system of the present invention having a composite filter medium including two (2) layers of the microbiological interception enhanced filter medium and two (2) layers of PLEKX® as described earlier.

Deionized water, approximately 500 ml, was passed through the filtration system to pre-wet the filter medium and verify that no bypass was occurring. Subsequently, 500 ml of the *E. coli* challenge, prepared in deionized water, was passed through the filter. The effluent was collected in a sterile Erlenmeyer flasks, diluted and plated on Petri dishes following standard procedures for *E. coli* and left overnight. After 24 hours, an additional 500 ml of deionized was passed through the system followed by another 500 ml *E. coli* challenge. This protocol was continued every 24 hours until the filter medium no longer provided an LRV above 4. The results are shown in Table XII below.

TABLE XII

Example 54: Efficacy Of A Filtration System Of The Present Invention With A 25.4 cm Water Column

| Total Amount of $H_2O$ (L) | Time in Use (hours) | No. of *E. coli* in Challenge | LRV | Flow Rate (ml/min.) |
|---|---|---|---|---|
| 1.0 | 0 | $9.33 \times 10^8$ | 8.99 | 28 |
| 2.0 | 24 | $7.86 \times 10^8$ | 8.89 | 32 |
| 3.0 | 48 | $2.86 \times 10^8$ | 8.46 | 27 |
| 4.0 | 72 | $1.35 \times 10^9$ | 8.37 | 21 |
| 5.0 | 96 | $1.18 \times 10^9$ | 8.07 | 17 |
| 6.0 | 120 | $8.4 \times 10^8$ | 7.38 | 18 |
| 7.0 | 144 | $1.09 \times 10^9$ | 4.95 | 12 |
| 8.0 | 168 | $3.6 \times 10^8$ | 3.50 | 16 |
| 9.0 | 192 | $6.13 \times 10^8$ | 3.61 | 12 |

The filtration system of Example 50 provided acceptable performance after 6.0 L of water had passed through the system at an average flow rate of about 24 ml/minute wherein the head pressure was caused by a 25.4 cm water column.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A filter system comprising:
   a granular bed of particles capable of removing charge-reducing contaminants;
   a microporous structure, disposed downstream from said granular bed, having a mean flow path of less than about 0.6 micron; and
   a microbiological interception enhancing agent comprising a silver-cationic material-halide complex having a high charge density, coated on at least a portion of a surface of said microporous structure.

2. The filter system of claim 1 wherein the particles comprise activated carbon.

3. The filter system of claim 1 wherein the particles comprise an anion exchange resin.

4. The filter system of claim 1 wherein said granular bed of particles further includes ingredients comprising activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, or combinations thereof.

5. The filter system of claim 1 wherein said microbiological interception enhancing agent consists of a silver-cationic material-halide complex wherein a homopolymer of diallyl dimethyl ammonium on a surface of said microporous structure has a halide counter ion associated therewith and wherein silver is precipitated with at least a portion of the halide counter ion.

6. The filter medium of claim 5 wherein the homopolymer of diallyl dimethyl ammonium halide has a molecular weight of greater than or equal to about 400,000 Daltons.

\* \* \* \* \*